(12) United States Patent
Pastan et al.

(10) Patent No.: US 7,816,087 B2
(45) Date of Patent: Oct. 19, 2010

(54) GENE EXPRESSED IN PROSTATE CANCER AND METHODS OF USE

(75) Inventors: Ira H. Pastan, Potomac, MD (US);
Tapan K. Bera, Germantown, MD (US);
Curt Wolfgang, Germantown, MD (US);
Byungkook Lee, Potomac, MD (US);
James Vincent, Takoma Park, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1541 days.

(21) Appl. No.: 10/495,663

(22) PCT Filed: Nov. 13, 2002

(86) PCT No.: PCT/US02/36648
§ 371 (c)(1),
(2), (4) Date: May 12, 2004

(87) PCT Pub. No.: WO03/042370
PCT Pub. Date: May 22, 2003

(65) Prior Publication Data
US 2004/0241702 A1    Dec. 2, 2004

Related U.S. Application Data

(60) Provisional application No. 60/336,308, filed on Nov. 14, 2001.

(51) Int. Cl.
    *G01N 33/53* (2006.01)
(52) U.S. Cl. .................................. 435/7.1; 530/350
(58) Field of Classification Search .................. 435/7.1; 530/350
    See application file for complete search history.

(56) References Cited

U.S. PATENT DOCUMENTS 6,268,170 B1 *  7/2001  Siddique et al. ............ 435/69.1

OTHER PUBLICATIONS

Stanton, P et al, 1994, Br J Cancer, 70: 427-433.*
Iehle, P et al, 1999, J Steroid Biochem Mol Biol, 68: 189-195.*
Kibel, AS et al, 2000, J urol, 164(1): 192-6.*
Zhau, HE, 1994, J Cell Biochem, Suppl 19: 208-216.*
Ren, C et al, 1998, Cancer Res, 58(6): 1285-90.*
Gingrich, JR et al, 1996, Cancer res, 56(18): 4096-4102.*
Russo, V et al, 1995, Int J Cancer, 64: 216-221.*
White et al, 2001 (Ann Rev Med, 52: 125-145).*
Boon, 1992 (Adv Can Res, 58:177-210).*
Smith RT, 1994 (Clin Immunol, 41(4): 841-849).*
Kirkin et al, 1998 (APMIS, 106: 665-679.*
Ezzell, 1995 (J. NIH Res, 7:46-49).*
Spitler, 1995 (Cancer Biotherapy, 10:1-3).*
Gura, 1997, (Science, 278:1041-1042).*
Jain, 1994 (Sci. Am., 271:58-65).*
Straub P et al, 1993, J Biol Chem 268(29): 21997-20003.*
Kouklis PD et al, 1993, J Cell Science, 106(pt 3): 919-28.*
Schmid S et al, 2001 (J comparative Neurology, 430(2): 160-71.*
Conner et al, 1996 (Mol Brain Res, 42: 1-17).*
Banki et al, 1994, JBC, 269 (4): 2847-51.*
Bendayan et al, 1995, J Histochem Cytochem, 43(9): 881-886).*
Bost et al, 1988, Immunol Investigation, 17 (6&7): 577-586).*
PCT/US 01/08631 in MPSRCH search result, 2007, us-10.495.663.1.rapm, result 7, p. 1.*
MPSRCH search result, 2007, us-10.495.663.1.rapm, result 7, p. 1.*
White et al, eds, Principles of Biochemistry, 1968, McGraw-Hill, New York, p. 148.*
Dong et al, 2000, Cancer Research, 60: 3880-3883.*
Walker et al, 1999, Genome Res, 9: 1198-1203.*
Genbank Accession No. AA573019.
Genbank Accession No. AA595369.
Genbank Accession No. AA613802.
Genbank Accession No. AC005237.
Genbank Accession No. AI620781.
Genbank Accession No. AI801934.
Genbank Accession No. BQ372536.
Genbank Accession No. CAA01837.
Genbank Accession No. NP_683148.
EMBL Accession No. AA573019, Sep. 11, 1997.
EMBL Accession No. AA595369, Sep. 24, 1997.
EMBL Accession No. AA613802, Oct. 13, 1997.
Genbank Accession No. AC005237, Sep. 30, 2000.
Genbank Accession No. AI620781, Apr. 26, 1999.

(Continued)

*Primary Examiner*—Larry R. Helms
*Assistant Examiner*—Minh-Tam Davis
(74) *Attorney, Agent, or Firm*—Klarquist Sparkman, LLP

(57) ABSTRACT

A new polypeptide is disclosed that is specifically detected in the cells of the prostate, termed Novel Gene Expressed in Prostate (NGEP). Polynucleotides encoding NGEP are also disclosed, as are vectors including these polynucleotides. Host cells transformed with these polynucleotides are also disclosed. Antibodies are disclosed that specfically bind NGEP. Methods are disclosed for using an NGEP polypeptide, an antibody that specifically binds NGEP, or a polynucleotide encoding NGEP. Assays are disclosed for the detection prostate cancer. Pharmaceutical compositions including an NGEP polypeptide, an antibody that specifically binds NGEP, or a polynucleotide encoding NGEP are also disclosed. These pharmaceutical compositions are of use in the treatment of prostate cancer.

9 Claims, 6 Drawing Sheets

OTHER PUBLICATIONS

Genbank Accession No. AI801934, Jul. 7, 1999.
Genbank Accession No. BQ372536, May 28, 2002.
Genbank Accession No. CAA01837, Oct. 17, 1995.
Genbank Accession No. NP_683148, Jan. 12, 2004.
Olsson, et al., "GDEP, a New Gene Differentially Expressed in Normal Prostate and Prostate Cancer," The Prostate, Laboratory of Molecular Biology, Division of Basic Sciences, National Cancer Institute, National Institutes of Health, Bethesda, Maryland, 48:231-241 (2001).
Vasmatzis, et al., "Discovery of Three Genes Specifically Expressed in Human Prostate by Expressed Sequence Tag Database Analysis," Proc. Natl. Acad. Sci. USA, vol. 95, pp. 300-304, Jan. 1998.
Bera, et al, "NGEP, a Gene Encoding a Membrane Protein Detected Only in Prostate Cancer and Normal Prostate," PNAS, vol. 101, No. 9, pp. 3059-3064, Mar. 2, 2004.

* cited by examiner

```
1
AAAGATAGATCCTGTCTCCAGGAGCCGGGAAGCCTCTGCCCTGGCCCAGCTGTGCTGTGGGCACCTCCCCTGC
CTGCTTCCTGGCCCACTTGCAGCCAAGGTGAGGGCAATGCCGAATGGCCACTGCCTGCCTGGGCGGGGC
TCCAAGGGCCACCCCTCCCCACCCTGTCCCGCAGTGAGGACGGACTCTACTGCCGAGACCAG
GCTCACGCGTGAGAGGTGGGCCATGACCTCCGAGACCCTCTTCCGGAAGCCACTGTGCCAGGAGCA
GGATGCTGCGGGCGACGGCCCAGGAAGAGGACACAGCACCGTCCTGATGTGAGCCCCCTGA
GGCAGAGAAGAGGGCTCTTACGGAGCACAGCCCTCGGAGCCAGGTGGACAGCAAGCG
GCCGCCTGCAGAGCTGGGAGTCCTGCCAAGCCCCGATCGACTTCGTCCTCGTTTGGGAGGAGG
ACCTGAAGCTAGACAGGCAGCAGGACAGTGCGCGGGACAGAACAGACATGCACAGGACCTG
GCGGGAGACTTTCTGGATAATCTTCGTGCGGGCCTGTGTGTAGACCAGTACGTGGAGGCT
GTCATGGGCAGGGCCCTAGGCCCTGCATCCACTCAGTGACCCATGACCTTGCCGCA TGAGGCCTG
AGGGCATGGTGTCCAGAGTCCCAGAGCAGATCAGGCCCAAAGTCCTGCTGGACCCCCAGCCACCGT
GAGCTCCGTGTGGCTAGGGAGCTGCTGTCCAGAGGCGGAGGTAAACATTGATCCCTCCTGCACACT
CAGCTCTCATGGAAGTCGGAGCCCTCAGGTCACCTGAAACTCGACACTACCTTTGCCATTCACCT
GTCCCGTCTCCAACATTAAAGCTTTTGGGTAGGCGAAAAAAAAAAAAAAAAAAAAAA
                                                  917

Nucleotide sequences of NGEP

ORF is in bold letters and the polyA site is underlined
```

FIG. 6

SEQUENCE LISTING

```
<160> NUMBER OF SEQ ID NOS: 10

<210> SEQ ID NO 1
<211> LENGTH: 179
<212> TYPE: PRT
<213> ORGANISM: Homo sapiens

<400> SEQUENCE: 1

Met Arg Met Ala Ala Thr Ala Trp Ala Gly Leu Gln Gly Pro Pro Leu
1               5                   10                  15

Pro Thr Leu Cys Pro Ala Val Arg Thr Gly Leu Tyr Cys Arg Asp Gln
            20                  25                  30

Ala His Ala Glu Arg Trp Ala Met Thr Ser Glu Thr Ser Ser Gly Ser
        35                  40                  45

His Cys Ala Arg Ser Arg Met Leu Arg Arg Arg Ala Gln Glu Glu Asp
    50                  55                  60

Ser Thr Val Leu Ile Asp Val Ser Pro Pro Glu Ala Glu Lys Arg Gly
65                  70                  75                  80
```

```
Ser Tyr Gly Ser Thr Ala His Ala Ser Glu Pro Gly Gly Gln Gln Ala
                85                  90                  95

Ala Ala Cys Arg Ala Gly Ser Pro Ala Lys Pro Arg Ile Asp Phe Val
            100                 105                 110

Leu Val Trp Glu Glu Asp Leu Lys Leu Asp Arg Gln Gln Asp Ser Ala
        115                 120                 125

Ala Arg Asp Arg Thr Asp Met His Arg Thr Trp Arg Glu Thr Phe Leu
    130                 135                 140

Asp Asn Leu Arg Ala Ala Gly Leu Cys Val Asp Gln Val Arg Gly Gly
145                 150                 155                 160

Cys His Gly Gln Gly Pro Arg Pro Cys Ile His Ser Val Thr His Asp
                165                 170                 175

Leu Ala Ala

<210> SEQ ID NO 2
<211> LENGTH: 917
<212> TYPE: DNA
<213> ORGANISM: Homo sapiens

<400> SEQUENCE: 2
aaaagataga tcctgctcca ggagccggga agcctcgccc tggccagctg tgctgggcac      60
ctcccctgcc tgcttcctgg cccacttgca ggcaaggtga gggcatgcga atggctgcca    120
ctgcctgggc ggggctccaa gggccacccc tccccaccct ctgtcccgca gtgaggacgg    180
gactctactg ccgagaccag gctcacgctg agaggtgggc catgacctcc gagacctctt    240
ccggaagcca ctgtgccagg agcaggatgc tgcggcgacg ggcccaggaa gaggacagca    300
ccgtcctgat cgatgtgagc ccccctgagg cagagaagag gggctcttac gggagcacag    360
cccacgcctc ggagccaggt ggacagcaag cggccgcctg cagagctggg agtcctgcca    420
agccccggat cgacttcgtc ctcgtttggg aggaggacct gaagctagac aggcagcagg    480
acagtgccgc ccgggacaga acagacatgc acaggacctg gcgggagact tttctggata    540
atcttcgtgc ggctgggctg tgtgtagacc aggtacgtgg aggctgtcat gggcagggcc    600
ctaggccctg catccactca gtgacccatg accttgccgc atgaggcctg agggcatggt    660
gtccagagtc ccagagcaga tcaggcccca aagtcctgct ggacccccca gccaccgtga    720
gctcctccgt gtggctaggg agctgctgtc cagaggcgga ggtaaacatt gatccctcct    780
gcacactcag ctctctcatg gaagtcggag ccctcagggt cacctgaaaa ctctgacact    840
acctttgcca ttcacctgtc ccgtctccaa cattaaagct tttgggtagg cgaaaaaaaa    900
aaaaaaaaaa aaaaaaa                                                  917

<210> SEQ ID NO 3
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 3
aagctagaca ggcagcagga ca                                              22

<210> SEQ ID NO 4
<211> LENGTH: 22
<212> TYPE: DNA
<213> ORGANISM: Artificial Sequence
<220> FEATURE:
<223> OTHER INFORMATION: Oligonucleotide primer
```

```
<400> SEQUENCE: 4
catgagagag ctgagtgtgc ag                                              22

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 5
gcctgatctg ctctgggact ctgg                                            24

<210> SEQ ID NO 6
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 6
acagcaccgt cctgatcgat gtgagc                                          26

<210> SEQ ID NO 7
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 7
tgtctagctt caggtcctcc tcccaaacg                                       29

<210> SEQ ID NO 8
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 8
gcttgctgtc cacctggctc cgaggc                                          26

<210> SEQ ID NO 9
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 9
aaagatagat cctgctccag gagccgg                                         27

<210> SEQ ID NO 10
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 10
gacaggtgaa tggcaaaggt gtcagag                                         27
```

GENE EXPRESSED IN PROSTATE CANCER AND METHODS OF USE

PRIORITY CLAIM

This is the §371 U.S. National Stage of International Application No. PCT/US2002/036648, filed Nov. 13, 2002, which was published in English under PCT Article 21(2), which in turn claims the benefit of U.S. Provisional Application No. 60/336,308, filed Nov. 14, 2001, which is incorporated by reference in its entirety.

FIELD OF THE INVENTION

This disclosure relates the prostate, specifically to polypeptides expressed specifically in the prostate. The disclosure further relates to detection and treatment of prostate cancer.

BACKGROUND OF THE INVENTION

Cancer of the prostate is the most commonly diagnosed cancer in men and is the second most common cause of cancer death (Carter and Coffey, *Prostate* 16:39-48, 1990; Armbruster et al., *Clinical Chemistry* 39:181, 1993). If detected at an early stage, prostate cancer is potentially curable. However, a majority of cases are diagnosed at later stages when metastasis of the primary tumor has already occurred (Wang et al., *Meth. Cancer Res.* 19:179, 1982). Even early diagnosis is problematic because not all individuals who test positive in these screens develop cancer.

Prostate specific antigen (PSA) is a 240 amino acid member of the glandular kallikrein gene family. (Wang et al., 1982, supra; Wang et al., *Invest. Urology*, 17:159, 1979; Bilhartz et al., *Urology*, 38:95, 1991). PSA is a serine protease, produced by normal prostatic tissue, and secreted exclusively by the epithelial cells lining prostatic acini and ducts (Wang et al., 1982, supra; Wang et al., 1979, supra; Lilja et al., *World J. Urol.*, 11:188-191, 1993). Prostate specific antigen can be detected at low levels in the sera of healthy males without clinical evidence of prostate cancer. However, during neoplastic states, circulating levels of this antigen increase dramatically, correlating with the clinical stage of the disease (Schellhammer et al., *Urologic Clinics of North America* 20:597, 1993; Huang et al., *Prostate* 23:201, 1993). Prostate specific antigen is now the most widely used marker for prostate cancer. However, there clearly is a need to identify additional antigens to aid in the diagnosis of prostate cancer, and for use as therapeutic agents.

Present treatment for prostate cancer includes radical prostatectomy, radiation therapy, or hormonal therapy. With surgical intervention, complete eradication of the tumor is not always achieved and the observed re-occurrence of the cancer (12-68%) is dependent upon the initial clinical tumor stage (Zietman et al., *Cancer* 71:959, 1993). Thus, alternative methods of treatment including prophylaxis or prevention are desirable.

Immunotherapy is a potent new weapon against cancer. Immunotherapy involves evoking an immune response against cancer cells based on their production of target antigens. Immunotherapy based on cell-mediated immune responses involves generating a cell-mediated response to cells that produce particular antigenic determinants, while immunotherapy based on humoral immune responses involves generating specific antibodies to cells that produce particular antigenic determinants.

Cancer cells produce various proteins that can become the target of immunotherapy; antigenic determinants normally present on a specific cell type can also be immunogenic. For example, Rosenberg et al. have shown that tumor infiltrating lymphocytes target and recognize antigenic determinants of the protein MART-1, produced by both normal melanocytes and malignant melanoma cells. Furthermore, active or passive immunotherapy directed against MART-1 or peptides of it that bind to MHC Class I molecules (epitopes of HLA A2, in particular) results in the destruction of melanoma cells as well as normal cells that produce MART-1 (Kawakami et al., *J. Immunol.* 21:237, 1998). The tissue specificity of PSA has made it a potential target antigen for active specific immunotherapy (Armbruster et al., *Clin. Chemistry* 39:181, 1993; Brawer et al., *Cancer Journal Clinic* 39:361, 1989), especially in patients who have undergone a radical prostatectomy in which the only PSA expressing tissue in the body should be in metastatic deposits.

Recent studies using in-vitro immunization have shown the generation of CD4 and CD8 cells specific for PSA (Peace et al., *Cancer Vaccines: Structural Basis for Vaccine Development* (Abstract), 1994; Correale et al., *9th International Congress of Immunology* (Abstract), 1995), and methods for inducing an immune response against PSA include the use of viral vectors incorporating DNA encoding PSA (e.g. see U.S. Pat. No. 6,165,460; Hodge et al., *Cancer* 63:231, 1995). Discovery of additional antigens expressed by the prostate gland can similarly be used to design immunotherapy methods for prostate cancer.

SUMMARY OF THE INVENTION

A new polypeptide is disclosed herein that is specifically detected in the cells of the prostate. This polypeptide is termed Novel Gene Expressed in Prostate (NGEP). Polynucleotides encoding NGEP are also disclosed herein, as are vectors including polynucleotides encoding NGEP, and host cells transformed with these polynucleotides. Antibodies that specifically bind NGEP are also disclosed.

Methods for using an NGEP polypeptide, an antibody that specifically binds NGEP, or a polynucleotide encoding NGEP are also disclosed. A specific, non-limiting example of a method of use is an assay to detect prostate cancer. Also disclosed are pharmaceutical compositions including an NGEP polypeptide, an antibody that specifically binds NGEP, or a polynucleotide encoding NGEP. In one embodiment, the pharmaceutical composition is used to treat prostate cancer.

The foregoing and other features and advantages will become more apparent from the following detailed description of several embodiments, which proceeds with reference to the accompanying figures.

BRIEF DESCRIPTION OF THE FIGURES

FIG. 2A is a digital image of a RNA hybridization of a multiple tissue dot-blot containing mRNA from 61 normal human cell types or tissues using NGEP cDNA as probe. NGEP expression is observed only in prostate (E8) and no detectable expression in brain (A1), heart (A4), lung (A8), kidney (A7), and pancreas (B9). FIG. 2B is a digital image of PCR on cDNAs from a panel of cDNAs isolated from several normal tissues including brain, heart, liver, lung, pancreas, and colon. The expected size of the NGEP PCR product is 176 bp. Lanes are: 1, no DNA; 2, DU145; 3, normal prostate; 4, prostate cancer; 5, prostate cancer; 6, brain; 7, heart; 8, kidney; 9, liver; 10, lung; 11, skeletal muscle; 12, normal prostate; 13, colon; 14, peripheral blood leukocyte; 15, small intestine; 16, ovary; 17, spleen; 18, thymus; 19, testis; 20, pancreas; and 21, placenta. FIG. 2C is a digital image of a Northern blot analysis of NGEP in different normal tissues. The matured transcript (shown by an arrow) is about 1.0 kb in size and is expressed only in prostate. The signal at the high molecular weight region is probably from the unspliced NGEP transcript. FIG. 2D is a digital image of aRT-PCR analysis of RNAs from prostate cancer cell line LnCAP and PC3. Lanes: M, molecular weight standard; 1, negative control; 2, PC3, 3, LnCAP; and 4, pNGEP plasmid positive control.

FIG. 3 shows the amino acid sequence of NGEP. NGEP is 179 amino acids in length, and has a predicted molecular weight of 19.6 kDa. Analysis of the amino acid sequence of NGEP protein was performed using the PROSITE program. Three possible casein kinase II phosphorylation sites are shown in rectangular boxes. One potential protein kinase C phosphorylation site is marked with one line whereas, the predicted camp-dependent protein kinase site is marked with two lines.

FIG. 5A is a digital image of in vitro translation of the NGEP cDNA. Expected 20 kDa protein product is detected in lane with NGEP cDNA. Lane with vector DNA alone showed no detectable bands. FIG. 5B is a digital image of a Western blot analysis of NGEP-transfected cell extract with anti-Myc-tag antibody. Two specific bands (20 and 24 kDa) are detected in cell extracts transfected with plasmid pNGEP-Myc. Cell extract from pPATE-Myc transfected cells is used as positive control and detects an expected size band of 16 kDa. FIGS. 5C and 5D are digital images of mmunocytochemical analysis of NGEP localization in transfected cells. Immunocytochemistry using anti-Myc antibody was done under confocal microscopy in LnCAP cells co-transfected with pEGFP and pNGEP-Myc. The signals representing NGEP expression were localized in both cytoplasim and nucleus (FIG. 5C). In a small fraction of positive cells (<5%), positive signals were found exclusively in cytoplasm (FIG. 5D).

FIG. 6 is the nucleotides sequence of the full-length (917 nucleotide) NGEP cDNA. The ORF is indicated in bold, and the poly A site is underlined.

SEQUENCE LISTING

Figure 1:
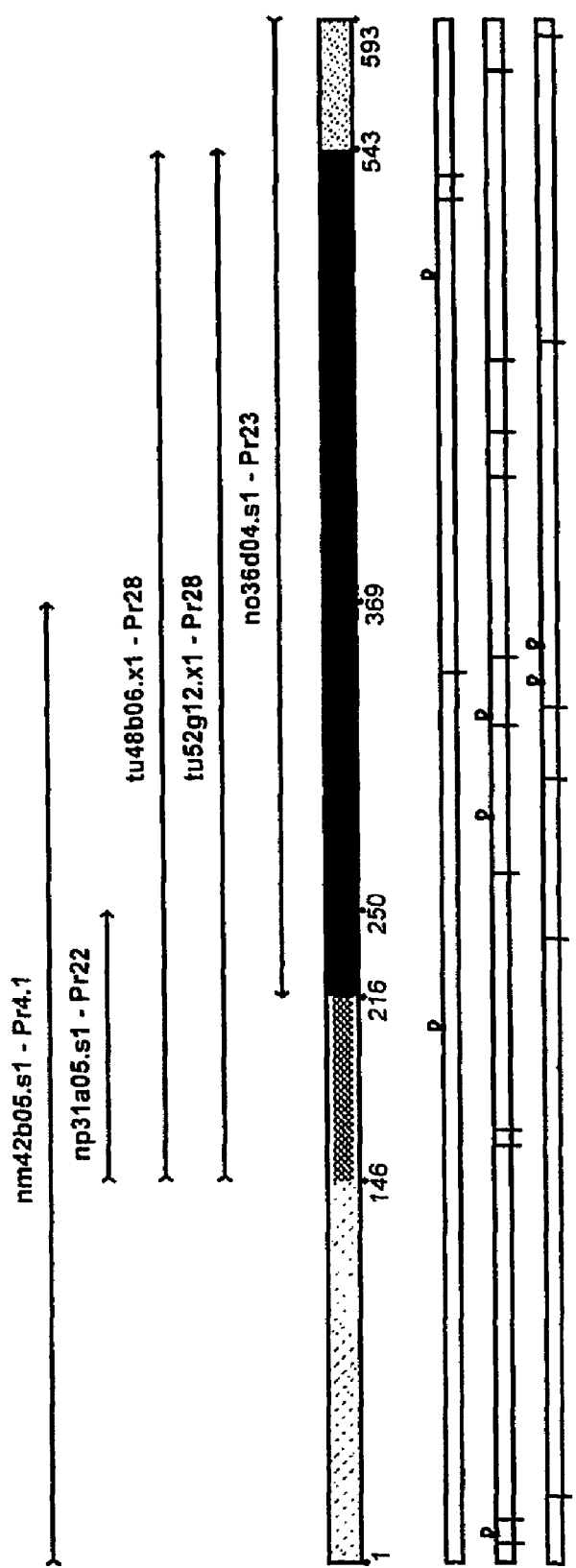
FIG. 1 is a schematic diagram of the CW-1 cluster, which was identified by computer analysis of the human EST database as a prostate specific cluster. There are 5 ESTs in this cluster of which 3 ESTs are from normal prostate and two ESTs are from prostate cancer (FIG. 1). All ESTs are localized at chromosome 2q37.3 on human genome. Pr4.1: Prostate cancer; Pr22: normal prostate; Pr28 normal prostate; Pr23 Prostate cancer.

The nucleic and amino acid sequences disclosed herein are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO:1 is the polypeptide sequence of an NGEP polypeptide.

SEQ ID NO:2 is the polynucleotide sequence of a polynucleotide encoding NGEP.

SEQ ID NO:3 is the sequence of the primer CW74.

SEQ ID NO:4 is the sequence of the primer CW75.

DETAILED DESCRIPTION OF SEVERAL EMBODIMENTS

A novel gene product expressed in cells of the normal prostate and prostate cancer, termed Novel Gene Expressed in Prostate (NGEP), is disclosed herein.

After defining some of the terms used herein, the discussion below sets forth the discovery of the nature of the NGEP protein, nucleic acid sequences encoding NGEP, and the expression of this protein. As NGEP is expressed in prostate cancer, it is of use in detecting prostate cancer cells. Diagnostic kits for NGEP are thus disclosed.

Antibodies that specifically bind NGEP are also disclosed herein. These antibodies are of use in detection assays, as well as in the production of immunoconjugates, such as immunotoxins, which can be used to target prostate cancer.

Nucleic acids encoding NGEP, or an NGEP polypeptide, can be used to produce an immune response against prostate cancer cells. Thus, pharmaceutical compositions including NGEP, or a nucleic acid encoding NGEP are also disclosed.

Terms

The following terms are provided to better define the present disclosure and to guide those of ordinary skill in the art in the practice of the methods described herein. Definitions of common terms can be found in Rieger et al., *Glossary of Genetics: Classical and Molecular*, 5th edition, Springer-Verlag: New York, 1991; and Lewin, *Genes V*, Oxford University Press: New York, 1994. The standard one- and three letter nomenclature for amino acid residues is used.

Additional explanations of terms commonly used in molecular genetics can be found in Benjamin Lewin, *Genes V* published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. Specific, non-limiting examples of a tissue specific antigen are a prostate specific antigen. A disease-specific antigen is expressed coincidentally with a disease process. Specific non-limiting examples of a disease-specific antigen are an antigen whose expression correlates with, or is predictive of, tumor formation, such as, prostate cancer. A disease specific antigen may be an antigen recognized by T cells or B cells.

Amplification: Of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Antibody: Immunoglobulin molecules and immunologically active portions of immunoglobulin molecules, i.e., molecules that contain an antigen binding site that specifically binds (immunoreacts with) an antigen. A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., Nature 341:544-546, 1989) which consists of a VH domain; (v) an isolated complimentarity determining region (CDR); and (vi) a F(ab')₂ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125, 023; Faoulkner et al., Nature 298:286, 1982; Morrison, J. Immunol. 123:793, 1979; Morrison et al., Ann Rev. Immunol 2:239, 1984).

Animal: Living multi-cellular vertebrate organisms, a category that includes, for example, mammals and birds. The term mammal includes both human and non-human mammals. Similarly, the term "subject" includes both human and veterinary subjects.

Conservative variants: "Conservative" amino acid substitutions are those substitutions that do not substantially affect or decrease an activity or antigenicity of NGEP. Specific, non-limiting examples of a conservative substitution include the following examples:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity or antigenicity.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Degenerate variant: A polynucleotide encoding an NGEP polypeptide that includes a sequence that is degenerate as a result of the genetic code. There are 20 natural amino acids, most of which are specified by more than one codon. Therefore, all degenerate nucleotide sequences are included in the invention as long as the amino acid sequence of the NGEP polypeptide encoded by the nucleotide sequence is unchanged.

Epitope: An antigenic determinant. These are particular chemical groups or peptide sequences on a molecule that are antigenic, i.e. that elicit a specific immune response. An antibody specifically binds a particular antigenic epitope on a polypeptide.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunoconjugate: A covalent linkage of an effector molecule to an antibody. The effector molecule can be an immunotoxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (e.g., domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule (EM). In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule.

Immunogenic peptide: A peptide which comprises an allele-specific motif or other sequence such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic composition: A composition comprising an NGEP polypeptide that induces a measurable CTL response against cells expressing NGEP polypeptide, or induces a measurable B cell response (e.g. production of antibodies that specifically bind NGEP) against an NGEP polypeptide. It further refers to isolated nucleic acids encoding an NGEP polypeptide that can be used to express the NGEP polypeptide (and thus be used to elicit an immune response against this polypeptide). For in vitro use, the immunogenic composition may consist of the isolated protein or peptide. For in vivo use, the immunogenic composition will typically comprise the protein or peptide in pharmaceutically acceptable carriers, and/or other agents. Any particular peptide, NGEP polypeptide, or nucleic acid encoding the polypeptide, can be readily tested for its ability to induce a CTL or B cell response by art-recognized assays.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, enzymatic linkages, and radioactive isotopes.

Lymphocytes: A type of white blood cell that is involved in the immune defenses of the body. There are two main types of lymphocytes: B-cells and T-cells.

Mammal: This term includes both human and non-human mammals. Similarly, the term "subject" includes both human and veterinary subjects.

Oligonucleotide: A linear polynucleotide sequence of up to about 100 nucleotide bases in length.

Open reading frame (ORF): A series of nucleotide triplets (codons) coding for amino acids without any internal termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Peptide: A chain of amino acids of between 3 and 30 amino acids in length. In one embodiment, a peptide is from about 10 to about 25 amino acids in length. In yet another embodiment, a peptide is from about 11 to about 20 amino acids in length. In yet another embodiment, a peptide is about 12 amino acids in length.

Peptide Modifications: NGEP polypeptides include synthetic embodiments of peptides described herein. In addition, analogues (non-peptide organic molecules), derivatives (chemically functionalized peptide molecules obtained starting with the disclosed peptide sequences) and variants (homologs) of these proteins can be utilized in the methods described herein. Each polypeptide of the invention is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ allyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of an NGEP polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included are mimetics prepared using such techniques.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single -and double-stranded forms of DNA.

Polypeptide: Any chain of amino acids, regardless of length or post-translational modification (e.g., glycosylation or phosphorylation). In one embodiment, the polypeptide is NGEP polypeptide.

Probes and primers: A probe comprises an isolated nucleic acid attached to a detectable label or reporter molecule. Primers are short nucleic acids, preferably DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise 20, 25, 30, 35, 40, 50 or more consecutive nucleotides.

Promoter: A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Specific, non-limiting examples of promoters include promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells Protein Purification: The NGEP polypeptides disclosed herein can be purified by any of the means known in the art. See, e.g., *Guide to Protein Purification*, ed. Deutscher, *Meth. Enzymol*. 185, Academic Press, San Diego, 1990; and Scopes, *Protein Purification: Principles and Practice*, Springer Verlag, N.Y., 1982. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Selectively hybridize: Hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g. RNA v. DNA) of the hybridizing regions of the nucleic acids can be considered in selecting hybridization conditions. An additional consideration is whether one of the nucleic acids is immobilized, for example, on a filter.

A specific, non-limiting example of progressively higher stringency conditions is as follows: 2×SSC/0.1% SDS at about room temperature (hybridization conditions); 0.2× SSC/0.1% SDS at about room temperature (low stringency conditions); 0.2×SSC/1.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual*, 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologues or variants of an NGEP polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math*. 2:482, 1981; Needleman and Wunsch, *J. Mol. Biol*. 48:443, 1970; Pearson and Lipman, *Proc. Natl. Acad. Sci. USA* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet*., 6:119, 1994 presents a detailed consideration of sequence alignment methods and homology calculations.

The NCBI Basic Local Alignment Search Tool (BLAST) (Altschul et al., *J. Mol. Biol*. 215:403, 1990) is available from several sources, including the National Center for Biotechnology Information (NCBI, Bethesda, Md.) and on the Internet, for use in connection with the sequence analysis programs blastp, blastn, blastx, tblastn and tblastx. A description of how to determine sequence identity using this program is available on the NCBI website on the internet.

Homologues and variants of an NGEP polypeptide are typically characterized by possession of at least 75%, for example at least 80%, sequence identity counted over the full length alignment with the amino acid sequence of NGEP using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologues and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologues could be obtained that fall outside of the ranges provided.

Specific binding agent: An agent that binds substantially only to a defined target. Thus an NGEP specific binding agent is an agent that binds substantially to an NGEP polypeptide. In one embodiment, the specific binding agent is a monoclonal or polyclonal antibody that specifically binds NGEP.

Subject: Living multi-cellular vertebrate organisms, a category that includes both human veterinary subjects, including human and non-human mammals.

T Cell: A white blood cell critical to the immune response. T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. CD8$^+$ T cells carry the "cluster of differentiation 8" (CD8) marker. In one embodiment, a CD8 T cells is a cytotoxic T lymphocytes. In another embodiment, a CD8 cell is a suppressor T cell.

Therapeutically active polypeptide: An agent, such as an NGEP polypeptide that causes induction of an immune response, as measured by clinical response (for example increase in a population of immune cells, production of antibody that specifically binds NGEP, or measurable reduction of tumor burden). Therapeutically active molecules can also be made from nucleic acids. Examples of a nucleic acid based therapeutically active molecule is a nucleic acid sequence that encodes an NGEP polypeptide, wherein the nucleic acid sequence is operably linked to a control element such as a promoter. Therapeutically active agents can also include organic or other chemical compounds that mimic the effects of NGEP.

The terms "therapeutically effective fragment of NGEP" or "therapeutically effective variant of NGEP" includes any fragment of NGEP, or variant of NGEP, that retains a function of NGEP, or retains an antigenic epitope of NGEP.

In one embodiment, a therapeutically effective amount of a fragment of NGEP is an amount used to generate an immune response, or to treat prostate cancer in a subject. Specific, non-limiting examples are the N-terminal half of NGEP or the C-terminal half of NGEP. Treatment refers to a therapeutic intervention that ameliorates a sign or symptom of prostate cancer, or a reduction in tumor burden.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. "Comprise" means "include." It is further to be understood that all base sizes or amino acid sizes, and all molecular weight or molecular mass values, given for nucleic acids or polypeptides are approximate, and are provided for description. Although methods and materials similar or equivalents to those described herein can be used in the practice or testing of the present disclosure, suitable methods and materials are described below. In case of conflict, the present specification, including explanations of terms, will control. In addition, the materials, methods, and examples are illustrative only and not intended to be limiting.

NGEP Polynucleotides and Polypeptides

Figure 5:
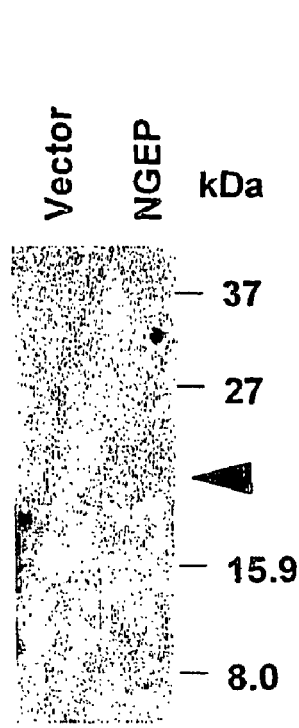
FIG. 5 is a set of digital images of the analysis and localization of protein product encoded by NGEP.
Figure 5:
Figure 5:
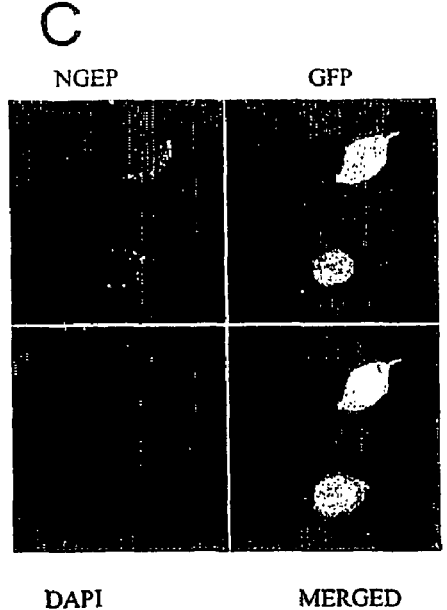
Figure 5:

Substantially purified Novel Gene Expressed in Prostate (NGEP) polypeptides are disclosed herein. In one embodiment, an NGEP polypeptide has a sequence 75%, 85%, 90%, 95%, or 99% homologous to the amino acid sequence set forth in SEQ ID NO:1 (see FIG. 5). In another embodiment, an NGEP polypeptide has a sequence as set forth a SEQ ID NO:1 or is a conservative variant of SEQ ID NO:1. In a further embodiment, an NGEP polypeptide has a sequence as set forth as SEQ ID NO:1. Fragments and variants of an NGEP polypeptide can readily be prepared by one of skill in the art using molecular techniques. In one embodiment, a fragment of an NGEP polypeptide includes at least 8, 10, 15, or 20 consecutive amino acids of an NGEP polypeptide. In another embodiment, a fragment of an NGEP polypeptide includes a specific antigenic epitope found on full-length NGEP.

One skilled in the art, given the disclosure herein, can purify NGEP polypeptide using standard techniques for protein purification. The substantially pure polypeptide will yield a single major band on a non-reducing polyacrylamide gel. The purity of the NGEP polypeptide can also be determined by amino-terminal amino acid sequence analysis.

Minor modifications of the NGEP polypeptide primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein.

Thus, specific, non-limiting examples of an NGEP polypeptide is a conservative variant of NGEP. A table of conservative substitutions is provided herein. Substitutions of the amino acids sequence shown in SEQ ID NO:1 can be made based on this table. Thus, one non-limiting example of a conservative variant is substitution of amino acid one (Met) of SEQ ID NO: 1 with an arginine residue. Similarly, another non-limiting example is substitution of amino acid 2 (Arg) of SEQ ID NO: 1 with a lysine residue. Using the sequence provided as SEQ ID NO:1, and the description of conservative amino acid substitutions provided, one of skill in the art can readily ascertain sequences of conservative variants. In several embodiments, a conservative variant includes at most one, at most two, at most five, at most ten, or at most fifteen conservative substitutions of the sequence shown in SEQ ID NO:1. Generally, a conservative variant will bind to antibodies that immunoreact with a polypeptide having a sequence set forth as SEQ ID NO:1.

One of skill in the art can readily produce fusion proteins including an NGEP polypeptide and a second polypeptide of interest. Optionally, a linker can included between the NGEP polypeptide and the second polypeptide of interest. Fusion proteins include, but are not limited to, a polypeptide including an NGEP polypeptide and a marker protein. In one embodiment, the marker protein can be used to identify or purify an NGEP polypeptide. Exemplary fusion proteins included, but are not limited to green fluorescent protein, six histidine residues, or myc and an NGEP polypeptide.

Polynucleotides encoding an NGEP polypeptide are also provided, and are termed NGEP polynucleotides. These polynucleotides include DNA, cDNA and RNA sequences which encode NGEP. It is understood that all polynucleotides encoding an NGEP polypeptide are also included herein, as long as they encode a polypeptide with the recognized activity, such as the binding to an antibody that recognizes an NGEP polypeptide. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of the NGEP polypeptide encoded by the nucleotide sequence is functionally unchanged. One specific, non-limiting example of a polynucleotide encoding NGEP is SEQ ID NO:2. Another specific non-limiting example of a polynucleotide encoding NGEP is a polynucleotide having at least 75%, 85%, 90%, 95%, or 99% homologous to SEQ ID NO:2 that encodes a polypeptide having an antigenic epitope or function of NGEP. Yet another specific non-limiting example of a polynucleotide encoding NGEP is a polynucleotide that encodes a polypeptide that is specifically bound by an antibody that specifically binds SEQ ID NO:1.

The NGEP polynucleotides include a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double forms of DNA. Also included in the invention are fragments of the above-described nucleic acid sequences that are and are at least 15 bases in length, which is sufficient to permit the fragment to selectively hybridize to DNA that encodes the disclosed NGEP polypeptide (e.g. a polynucleotide that encodes SEQ ID NO:1) under physiological conditions. The term "selectively hybridize" refers to hybridization under moderately or highly stringent conditions, which excludes non-related nucleotide sequences. The NGEP polynucleotide sequence disclosed herein include, but are not limited to, SEQ ID NO:2, degenerate variants of SEQ ID NO:2, and sequences that encode conservative variations of NGEP polypeptide.

DNA sequences encoding NGEP polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

NGEP polynucleotide sequences can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding NGEP may be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with NGEP polynucleotide sequences, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Isolation and purification of recombinantly expressed polypeptide may be carried out by conventional means including preparative chromatography and immunological separations.

Antibodies

An NGEP polypeptide or a fragment or conservative variant thereof can be used to produce antibodies which are immunoreactive or bind to an epitope of NGEP. Polyclonal antibodies, antibodies which consist essentially of pooled monoclonal antibodies with different epitopic specificities, as well as distinct monoclonal antibody preparations are included.

The preparation of polyclonal antibodies is well-known to those skilled in the art. See, for example, Green et al., "Production of Polyclonal Antisera, in: *Immunochemical Protocols* pages 1-5, Manson, ed., Humana Press 1992; Coligan et al., "Production of Polyclonal Antisera in Rabbits, Rats, Mice and Hamsters, in: *Current Protocols in Immunology*, section 2.4.1, 1992.

The preparation of monoclonal antibodies likewise is conventional. See, for example, Kohler & Milstein, *Nature* 256: 495, 1975; Coligan et al., sections 2.5.1-2.6.7; and Harlow et al., in: *Antibodies: a Laboratory Manual*, page 726, Cold Spring Harbor Pub., 1988. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1-2.7.12 and sections 2.9.1-2.9.3; Barnes et al., Purification of Immunoglobulin G (IgG), in: *Methods in Molecular Biology*, Vol. 10, pages 79-104, Humana Press, 1992.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies can also be derived from subhuman primate antibody. General techniques for raising therapeutically useful antibodies in baboons can be found, for example, in WO 91/11465, 1991, and Losman et al., *Int. J. Cancer* 46:310, 1990.

Alternatively, an antibody that specifically binds an NGEP polypeptide can be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833, 1989. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. USA* 89:4285, 1992; Sandhu, *Crit. Rev. Biotech.* 12:437, 1992; and Singer et al., *J. Immunol.* 150:2844, 1993.

Antibodies can be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994. Cloning and expression vectors that are useful for producing a human immunoglobulin phage library can be obtained, for example, from STRATAGENE Cloning Systems (La Jolla, Calif.).

In addition, antibodies can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994.

Antibodies include intact molecules as well as fragments thereof, such as Fab, F(ab')$_2$, and Fv which are capable of binding the epitopic determinant. These antibody fragments retain some ability to selectively bind with their antigen or receptor and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody (SCA), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch. Biochem. Biophys*. 89:230, 1960; Porter, *Biochem. J*. 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent (Inbar et al., *Proc. Nat'l Acad. Sci. USA* 69:2659, 1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick et al., *Methods: a Companion to Methods in Enzymology*, Vol. 2, page 106, 1991).

Antibodies can be prepared using an intact polypeptide or fragments containing small peptides of interest as the immunizing antigen. The polypeptide or a peptide used to immunize an animal can be derived from substantially purified polypeptide produced in host cells, in vitro translated cDNA, or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, *Current Protocols in Immunology*, Wiley Interscience, 1991).

It is also possible to use the anti-idiotype technology to produce monoclonal antibodies which mimic an epitope. For example, an anti-idiotypic monoclonal antibody made to a first monoclonal antibody will have a binding domain in the hypervariable region that is the "image" of the epitope bound by the first monoclonal antibody.

Binding affinity for a target antigen is typically measured or determined by standard antibody-antigen assays, such as competitive assays, saturation assays, or immunoassays such as ELISA or RIA. Such assays can be used to determine the dissociation constant of the antibody. The phrase "dissociation constant" refers to the affinity of an antibody for an antigen. Specificity of binding between an antibody and an antigen exists if the dissociation constant ($K_D=1/K$, where K is the affinity constant) of the antibody is, for example <1 µM, <100 nM, or <0.1 nM. Antibody molecules will typically have a $K_D$ in the lower ranges. $K_D=[Ab-Ag]/[Ab][Ag]$ where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible noncovalent associations such as electrostatic attraction, Van der Waals forces and hydrogen bonds.

Effector molecules, e.g., therapeutic, diagnostic, or detection moieties can be linked to an antibody that specifically binds NGEP, using any number of means known to those of skill in the art. Exemplary effector molecules include, but not limited to, a radiolabels, fluorescent markers, or toxins (e.g. *Pseudomonas* exotoxin (PE), see "Monoclonal Antibody-Toxin Conjugates: Aiming the Magic Bullet," Thorpe et al., "Monoclonal Antibodies in Clinical Medicine", Academic Press, pp. 168-190, 1982; Waldmann, *Science*, 252: 1657, 1991; U.S. Pat. Nos. 4,545,985 and 4,894,443, for a discussion of toxins and conjugation). Both covalent and noncovalent attachment means may be used. The procedure for attaching an effector molecule to an antibody varies according to the chemical structure of the effector. Polypeptides typically contain a variety of functional groups; e.g., carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In view of the large number of methods that have been reported for attaching a variety of radiodiagnostic compounds, radiotherapeutic compounds, label (e.g. enzymes or fluorescent molecules) drugs, toxins, and other agents to antibodies one skilled in the art will be able to determine a suitable method for attaching a given agent to an antibody or other polypeptide.

Therapeutic Methods and Pharmaceutical Compositions

An NGEP polypeptide can be administered to a subject in order to generate an immune response. In one embodiment, a therapeutically effective amount of an NGEP polypeptide is administered to a subject to treat prostate cancer. In exemplary applications, compositions are administered to a patient suffering from a disease, such as prostate cancer, in an amount sufficient to raise an immune response to NGEP-expressing cells. Administration induces a sufficient immune response to slow the proliferation of such cells or to inhibit their growth. Amounts effective for this use will depend upon the severity of the disease, the general state of the patient's health, and the robustness of the patient's immune system. A therapeutically effective amount of the compound is that which provides either subjective relief of a symptom(s) or an objectively identifiable improvement as noted by the clinician or other qualified observer.

An NGEP polypeptide can be administered by any means known to one of skill in the art (see Banga, A., Parenteral Controlled Delivery of Therapeutic Peptides and Proteins, in *Therapeutic Peptides and Proteins*, Technomic Publishing Co., Inc., Lancaster, Pa., 1995) such as by intramuscluar, subcutaneous, or intravenous injection, but even oral, nasal, or anal administration is contemplated. In one embodiment, administration is by subcutaneous or intramuscular injection. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, e.g., Banja, supra). A particulate carrier based on a synthetic polymer has been shown to act as an adjuvant to enhance the immune response, in addition to providing a controlled release. Aluminum salts may also be used as adjuvants to produce a humoral immune response. Thus, in one embodiment, an NGEP polypeptide is administered in a manner to induce a humoral response.

In another embodiment, an NGEP polypeptide is administered in a manner to direct the immune response to a cellular response (that is, a CTL response), rather than a humoral (antibody) response. A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (e.g., via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinly-seryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, the two compositions can be combined to elicit both humoral and cell-mediated responses where that is deemed desirable.

In yet another embodiment, to induce a CTL response to an immunogenic NGEP polypeptide or fragment thereof, a MRC class II-restricted T-helper epitope is added to the CTL antigenic peptide to induce T-helper cells to secrete cytokines in the microenvironment to activate CTL precursor cells. The technique further involves adding short lipid molecules to retain the construct at the site of the injection for several days to localize the antigen at the site of the injection and enhance its proximity to dendritic cells or other "professional" antigen presenting cells over a period of time (see Chesnut et al., "Design and Testing of Peptide-Based Cytotoxic T-Cell-Mediated Immunotherapeutics to Treat Infectious Diseases and Cancer," in Powell et al., eds., *Vaccine Design, the Subunit and Adjuvant Approach*, Plenum Press, New York, 1995).

A pharmaceutical composition including an NGEP polypeptide is thus provided. In one embodiment, the NGEP polypeptide, or fragment thereof, is mixed with an adjuvant containing two or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly (oxy-1,2-ethanediyl; manufactured by ICI Americas, Wilmington, Del.), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, preferably at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, J. Am. Oil. Chem. Soc. 54:110 (1977), and Hunter et al., J. Immunol 129:1244 (1981), PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, J. Immun. 133:3167 (1984). The agent can be provided in an effective amount, for example between 0.5 and 10%, most preferably in an amount between 1.25 and 5%.

The oil included in the composition is chosen to promote the retention of the antigen in oil-in-water emulsion, i.e., to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, most preferably between 2.5 and 5%. The oil should be both biodegradable and biocompatible so that the body can break down the oil over time, and so that no adverse affects, such as granulomas, are evident upon use of the oil.

An adjuvant can be included in the composition. In one embodiment, the adjuvant is a mixture of stabilizing detergents, micelle-forming agent, and oil available under the name Provax® (IDEC Pharmaceuticals, San Diego, Calif.).

In another emobodiment, a pharmaceutical composition includes a nucleic acid encoding an NGEP polypeptide or immunogenic fragment thereof. A therapeutically effective amount of the NGEP polynucleotide can be administered to a subject in order to generate an immune response. In one specific, non-limiting example a therapeutically effective amount of the NGEP polynucleotide is administered to a subject to treat prostate cancer.

One approach to administration of nucleic acids is direct immunizaiton with plasmid DNA, such as with a mammalian expression plasmid. As described above, the nucleotide sequence encoding NGEP, or an immunogenic peptide thereof, can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response) and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce class I mediated CTL responses (Takahashi et al., *Nature* 344:873, 1990).

In another approach to using nucleic acids for immunization, an NGEP polypeptide or an immunogenic peptide thereof can also be expressed by attenuated viral hosts or vectors or bacterial vectors. Recombinant vaccinia virus, adeno-associated virus (AAV), herpesvirus, retrovirus, or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456460, 1991).

In one embodiment, a nucleic acid encoding an NGEP polypeptide or an immunogenic fragment thereof is introduced directly into cells. For example, the nucleic acid may be loaded onto gold microspheres by standard methods and introduced into the skin by a device such as Bio-Rad's Helios™ Gene Gun. The nucleic acids can be "naked," consisting of plasmids under control of a strong promoter. Typically, the DNA is injected into muscle, although it can also be injected directly into other sites, including tissues in proximity to metastases. Doseages for injection are usually around 0.5 μg/kg to about 50 mg/kg, and typically are about 0.005 mg/kg to about 5 mg/kg (see, e.g., U.S. Pat. No. 5,589,466).

In addition, the cell growth inhibiting chimeric molecules including an antibody that specifically binds NGEP linked to a toxin (i.e., PE linked to an anti-NGEP antibody), can be prepared in pharmaceutical compositions. These cell growth inhibiting moleucles can be administered by any method known to one of skill in the art. For example, to treat prostate cancer, the pharmaceutical compositions of this invention can be administered directly into the prostate gland. Metastases of prostate cancer may be treated by intravenous administration or by localized delivery to the tissue surrounding the tumor.

The compositions for administration will commonly comprise a solution of the cell growth inhibiting chimeric molecules dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of cell growth inhibiting molecules in these formulations can vary widely, and will be selected primarily based on fluid volumes, viscosities, body weight and the like in accordance with the particular mode of administration selected and the patient's needs.

In one specific, non-limiting example, a pharmaceutical composition for intravenous administration, such as an immunotoxin, would be about 0.1 to 10 mg per patient per day. Dosages from 0.1 up to about 100 mg per patient per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as Remingtons Phamaceutical Sciences, $19^{th}$ Ed., Mack Publishing Company, Easton, Pa. (1995).

The compositions can be administered for therapeutic treatments. In therapeutic applications, compositions are administered to a patient suffering from a disease, such as prostate cancer, in a therapeutically effective amount, which is an amount sufficient to cure or at least partially arrest the disease or a sign or symptom of the disease. Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In one embodiment, the dosage is administered once as a bolus, but in another embodiment can be applied periodically until either a therapeutic result is achieved. Generally, the dose is sufficient to treat or ameliorate symptoms or signs of disease without producing unacceptable toxicity to the patient.

Controlled release parenteral formulations of cell growth inhibiting chimeric molecules can be made as implants, oily injections, or as particulate systems. For a broad overview of protein delivery systems (see Banga, A. J., Therapeutic Peptides and Proteins: Formulation, Processing, and Delivery Systems, Technomic Publishing Company, Inc., Lancaster, Pa., 1995). Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, J., Colloidal Drug Delivery Systems, J. Kreuter, ed., Marcel Dekker, Inc., New York, N.Y., pp. 219-342, 1994; Tice & Tabibi, Treatise on Controlled Drug Delivery, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, R., *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992); and Pec et al., *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri, et al., Liposome Drug Delivery Systems, Technomic Publishing Co., Inc., Lancaster, Pa., 1993). Numerous additional systems for controlled delivery of therapeutic proteins are known (e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496).

In another method, antigen presenting cells (APCs) are pulsed or co-incubated with peptides comprising an epitope from NGEP in vitro. These cells are used to sensitize CD8 cells, such as tumor infiltrating lymphocytes from prostate cancer tumors or peripheral blood lymphocytes. The TILs or PBLs preferably are from the subject. However, they should at least be MHC Class-I restricted to the HLA types the subject possesses. An effective amount of the sensitized cells are then administered to the subject.

PBMCs may be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived.

The cells can be administered to inhibit the growth of cells of NGEP expressing tumors. In these applications, a therapeutically effective amount of activated antigen presenting cells, or activated lymphocytes, are administered to a subject suffering from a disease, in an amount sufficient to raise an immune response to NGEP-expressing cells. The resulting immune response is sufficient to slow the proliferation of such cells or to inhibit their growth.

In a supplemental method, any of these immunotherapies is augmented by administering a cytokine, such as IL-2, IL-3, IL-6, IL-10, L-12, IL-15, GM-CSF, interferons.

Diagnostic Methods and Kits

A method is provided herein for the detection of NGEP-expressing prostate cells or prostate tissue in a biological sample. The sample can be any sample that includes NGEP polypeptide or a nucleic acid encoding NGEP polypeptide. Such samples include, but are not limited to, tissue from biopsies, autopsies, and pathology specimens. Biological samples also include sections of tissues, such as frozen sections taken for histological purposes. Biological samples further include body fluids, such as blood, sputum, serum, or urine. A biological sample is typically obtained from a mammal, such as a rat, mouse, cow, dog, guinea pig, rabbit, or primate. In one embodiment the primate is macaque, chimpanzee, or a human. In a further embodiment the subject has prostate cancer, or is suspected of having prostate cancer. Methods of detection include, for example, radioimmunoassay, sandwich immunoassays (including ELISA), immunofluorescence assays, Western blot, affinity chromatography (affinity ligand bound to a solid phase), and in situ detection with labeled antibodies.

In one embodiment, a method is provided for detecting an NGEP polypeptide. Kits for detecting an NGEP polypeptide of fragment thereof will typically comprise an antibody that specifically binds NGEP. In some embodiments, an antibody fragment, such as an Fv fragment is included in the kit. For in vivo uses, the antibody is preferably an scFv fragment. In a further embodiment the antibody is labeled (e.g. fluorescent, radioactive, or an enzymatic label).

In one embodiment, a kit includes instructional materials disclosing means of use of an antibody that specifically binds an NGEP polypeptide or fragment thereof (e.g. for detection of NGEP expressing cells in a sample). The instructional materials may be written, in an electronic form (e.g. computer diskette or compact disk) or may be visual (e.g. video files). The kits may also include additional components to facilitate the particular application for which the kit is designed. Thus, for example, the kit may additionally contain means of detecting a label (e.g. enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment of the present invention, the diagnostic kit comprises an immunoassay. Although the details of the immunoassays may vary with the particular format employed, the method of detecting an NGEP polypeptide or fragment thereof in a biological sample generally comprises the steps of contacting the biological sample with an antibody which specifically reacts, under immunologically reactive conditions, to NGEP. The antibody is allowed to specifically bind under immunologically reactive conditions to form an immune complex, and the presence of the immune complex (bound antibody) is detected directly or indirectly.

In an alternative set of embodiments, kits can be provided for detecting nucleic acids encoding NEGP or a fragment thereof in a biological sample. For example, sample from a subject can be tested to determine whether nucleic acids encoding NGEP protein are present. In one embodiment, an amplification procedure is utilized to detect nucleic acids encoding NGEP. In another embodiment, a blotting procedure (e.g. Northern Blot or Dot Blot) is used to detect the presence of nucleic acids encoding NGEP. Thus, a kit can include probes or primers that specifically hybridize to nucleic acids encoding NGEP.

In one embodiment, a kit provides a primer that amplifies nucleic acid encoding NGEP. Conveniently, the amplification is performed by polymerase chain reaction (PCR). A number of other techniques are, however, known in the art and are contemplated for use. For example, Marshall, U.S. Pat. No. 5,686,272, discloses the amplification of RNA sequences using ligase chain reaction, or "LCR," (Landegren et al., *Science* 241:1077, 1988); Wu et al., Genomics, 4:569, 1989; Barany, in *PCR Methods and Applications* 1:5, 1991); and Barany, *Proc. Natl. Acad. Sci. USA* 88:189, 1991). Or, the RNA can be reverse transcribed into DNA and then amplified by LCR, PCR, or other methods. An exemplar protocol for conducting reverse transcription of RNA is taught in U.S. Pat. No. 5,705,365. Selection of appropriate primers and PCR protocols are taught, for example, in Innis, M. et al., eds., PCR Protocols 1990 (Academic Press, San Diego Calif.).

In one embodiment, the kit includes instructional materials disclosing means of use for the primer or probe. The kits may also include additional components to facilitate the particular application for which the kit is designed. The kits may additionally include buffers and other reagents routinely used for the practice of a particular method. Such kits and appropriate contents are well known to those of skill in the art.

The invention is illustrated by the following non-limiting Examples.

EXAMPLES

Example 1

Computer Analysis of EST Sequences

The NCBI dbEST/CGAP database (see Emmert-Buck et al., *Science* 274:998, 1996; Krizman, D. B. et al., *Cancer Res.* 56:5380, 1996); Strausberg, R. L. et al., *Nat. Genet.* 16:415, 1997), was used as a source for cDNA sequences. The ESTs from human tissues and tumors were downloaded from the NCBI EST database. The cDNA libraries that we processed are listed in several websites, including the Unigene Cluster from the NCBI website, amongst others. The EST sequences were clustered and sorted as described before (Vasmatzis, G. et al., *Proc. Natl. Acad. Sci., USA* 95:300, 1998). However, the candidate gene list was updated by using the EST dataset of, May 2000. Two updated candidate lists were prepared, one with the specificity cutoff for prostate of three as before and another with the cutoff value of six.

The cluster CW-1 is identified by computer analysis of the human EST database as a prostate specific cluster. There are 5 ESTs in this cluster of which 3 ESTs are from normal prostate and two ESTs are from prostate cancer (FIG. 1). All ESTs are localized at chromosome 2q37.3 on human genome.

Example 2

Specificity of CW-1 Cluster

To determine the tissue specificity of the CW-1 cluster experimentally, a multi-tissue dot blot analysis was performed using a PCR generated DNA fragment from the cluster as a probe.

The human multiple tissue RNA blot (RNA Masterblot, Clontech, Palo Alto, Calif.) and Northern blot (Multiple Tissue Northern blot, Human II, Clontech) hybridizations were carried out as described previously (Liu et al., *Biochem. Biophys. Res. Commun.*, 264:833, 1999). Briefly, RNA hybridizations with multiple tissue RNA dot-blot and northern blot were performed as follows: membranes were pre-hybridized for 2 h in hybridization solution (Hybrisol I; Intergen, Purchase, N.Y.) at 45° C.

The cDNA probe was produced from a PCR fragment generated using the primer pair CW74: (SEQ ID NO: 3, AAG CTA GAC AGG CAG CAG GAC A) and CW75 (SEQ ID NO:4, CATGAG AGA GCT GAG TGT GCA G; CW91: SEQ ID NO: 5, GCC TGA TCT GCT CTG GGA CTC TGG), and was labeled with $^{32}$P by random primer extension (Lofstrand Labs Ltd, Gaithersburg, Md.), added to the membranes and hybridized for 16 hours. The membranes were then washed 2×15 minutes in 2×SSC, 0.1% SDS, at room temperature and then washed 2×15 minutes in 0.5×SSC, 0.1 %SDS, at 55° C. Finally the membranes were exposed on x-ray film for 1-2 days. The washing and the autoradiography of the blot were performed as described (Bera et al., *Proc. Natl. Acad. Sci. USA* 99: 3058-3063, 2002).

Figure 2:
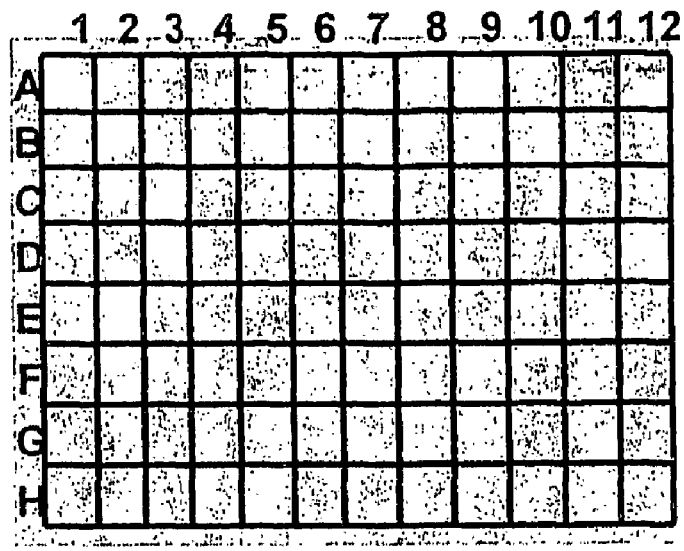
FIG. 2 is a set of digital images showing tissue specific expression of NGEP mRNA.
Figure 2:
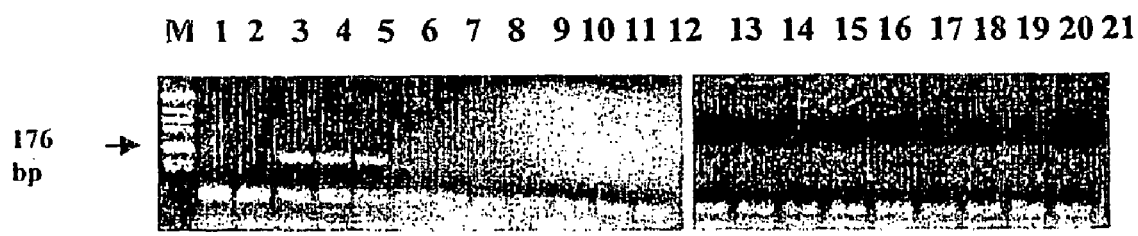
Figure 2:
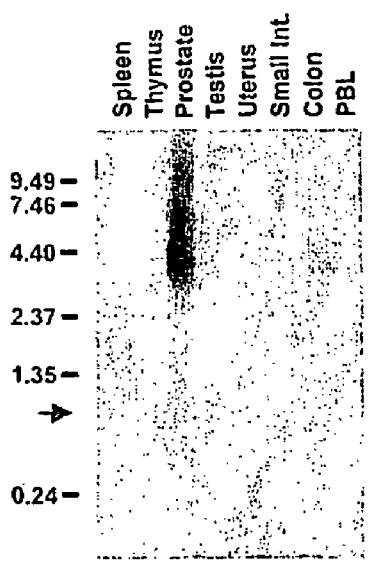
Figure 2:
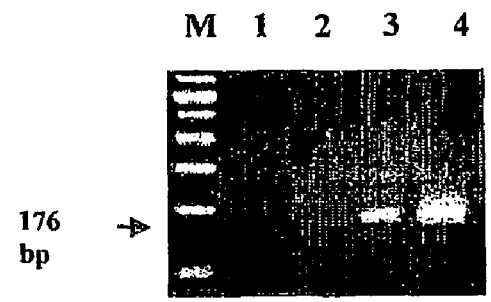

As shown in FIG. 2A, among the 76 different samples of normal and fetal tissue examined, CW-1 is detected strongly only in prostate sample. The expression of the CW-1 cluster is not detectable in any other tissues including essential organs including brain (A1), heart (A4), lung (A8), kidney (A7), and pancreas (B9). Dot-blot analysis is not a very sensitive technique and often gave a negative signal for genes, which are expressed at a very low level. To validate the result obtained from the dot-blot analysis, a more sensitive RT-PCR method was used for the expression analysis of CW-1 cluster. A panel of cDNAs isolated from several normal tissues including brain, heart, liver, lung, pancreas, colon, was used for PCR with a primer pair designed from the sequence of the CW-1 cluster. As shown in FIG. 2B, a specific band of 176 bp in size is detected only in prostate (two normal, lanes 3 and 12; two cancer, lanes 4 and 5) tissue indicating the CW-1 cluster is specifically expressed in prostate. Because of its specific expression in prostate, this sequence was named NGEP (New Gene Expressed in Prostate).

To determine the expression of NGEP in prostate cancer cell lines, an RT-PCR analysis was performed using RNAs from three prostate cancer cell line LnCAP, and PC3. NGEP expression was detected only in the RNA from LnCAP cells but not in PC3 (FIG. 2D).

Example 3

Full Length cDNA Cloning of CW-1

To determine the transcript size of the CW-1 cluster in tissues, an analysis was made of a Northern blot containing mRNAs from different tissues including prostate. The PCR generated probe that was used for the dot blot analysis was also used in this experiment. Methods are described in Example 2.

As shown in FIG. 2C, several bands of different sizes are detected only in prostate lane. The smallest band, which likely is the mature mRNA, is about 900 base pairs (bp) in size (arrow). The high molecular weight bands which are detected by the probe are probably unspliced variants of the transcript or transcripts with longer 3' untranslated regions.

To isolate the full-length cDNA for CW-1 a 5' and 3' RACE PCR method was employed to isolate a clone of 917 bp in size (see FIG. 6).

The primers used in this study were synthesized by Lofstrand Lab, (Gaithersburg, Md.) and the nucleotide sequences of the primers are as follows: Ngepex25, ACAGCA CCG TCC TGA TCG ATG TGA GC (SEQ ID NO: 6); Ngep3-2, TGT CTA GCT TCA GGT CCT CCT CCC AAA CG (SEQ ID NO: 7); CW88, GCT TGC TGT CCA CCT GGC TCC GAG GC (SEQ ID NO: 8); T420, AAA GAT AGA TCC TGC TCC AGG AGC CGG (SEQ ID NO: 9); T421, GAC AGGTGA ATG GCA AAG GTG TCA GAG (SEQ ID NO: 10).

Rapid amplification of cDNA ends (RACE) was performed on Marathon Ready normal prostate cDNA (Clontech, Palo Alto, Calif.) and on total RNA from a prostate cancer sample (prepared using Trizol, Life Technologies) The RACE PCR on the total RNA sample was made using the SMART RACE cDNA amplification kit (Clontech, Palo Alto, Calif.). The gene specific primer CW88 was used for the RACE-PCR reaction with adopter primer AP1 as recommended in the kit. The PCR product was gel purified and cloned into the pCR2.1 TOPO TA cloning vector (Invitrogen, Carlsbad, Calif.). The positive clones were identified by restriction digestion using Eco RI and selective clones are sequenced using Perkin-Elmer's dRhodamine terminator sequencing kit (Perkin-Elmer Applied System, Warrington, UK). Finally, the full-length NGEP was cloned by PCR using the sequence information from the RACE clones. The PCR primers used for the full-length NGEP cloning were T420 and T421.

Figure 3:
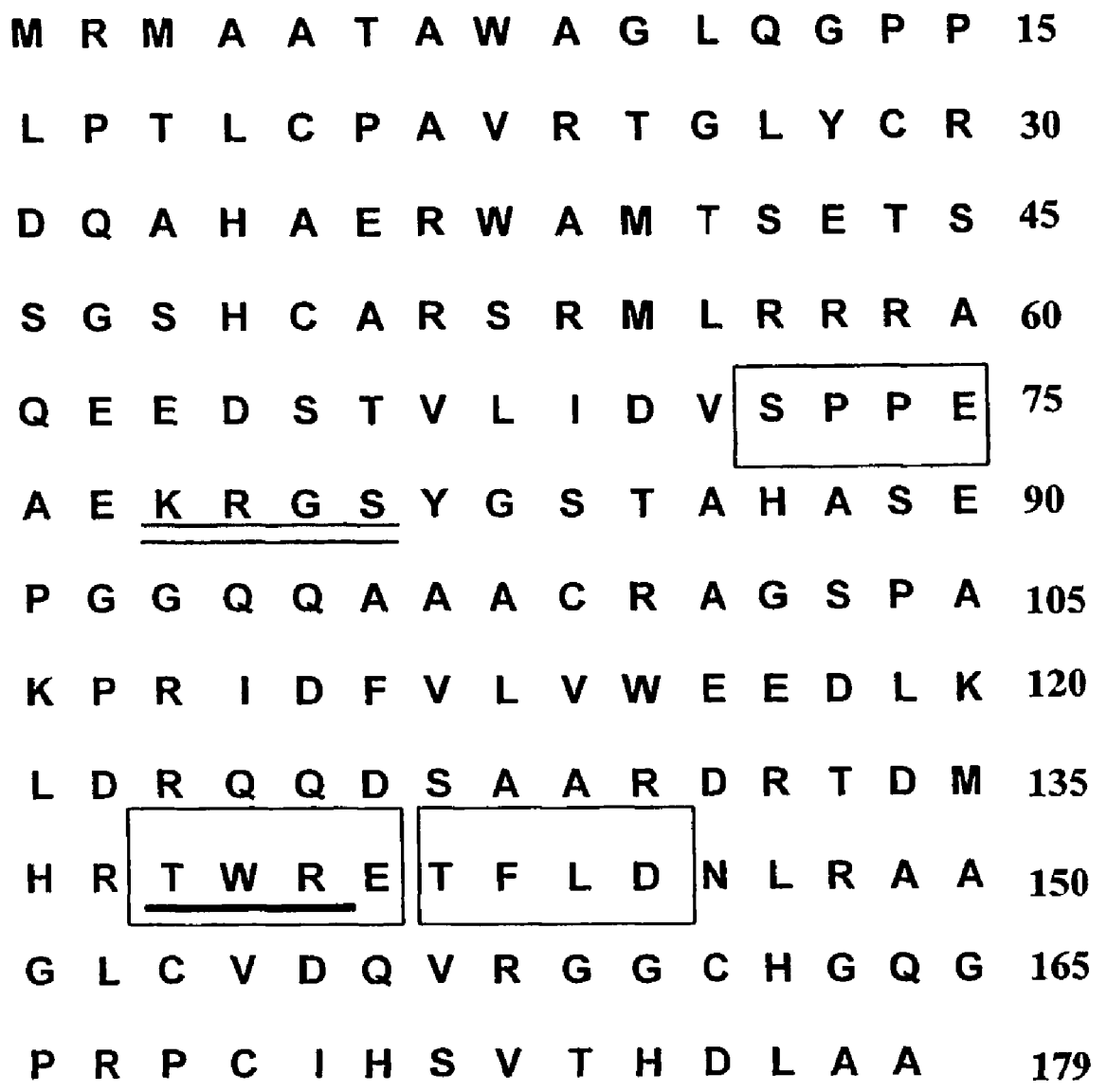

A 5' and 3' RACE PCR method was used to isolate a clone of 917 base pairs in size. The complete nucleotide sequence of the cDNA reveals that it has an open reading frame of 179 amino acids (FIGS. 3 and 6). The nucleotide sequence analysis of the full-length cDNA revels that it is a new gene with no significant sequence similarity with known genes in the database. The calculated molecular weight of the protein encoded by the NGEP cDNA is about 19.6 kDa.

Example 4

NGEP mRNA is Expressed in Epithelial Cells of Normal Prostate and Prostate Cancer To determine the cell types in normal prostate and prostate cancer that express NGEP mRNA, in situ hybridization was performed using a biotin labeled NGEP cDNA as a probe.

Briefly, biotinylated probes used for the in situ hybridization were prepared using the full-length NGEP cDNA cloned in TOPO TA cloning vector. Full-length U6 cDNA cloned in same vector was used as positive control. Probe labeling, pretreatment of the tissue section, hybridization, and washing conditions were similar to those described previously (Bera et al., *Proc. Natl. Acad. Sci. USA* 99: 6997-7002, 2002). Microscopic evaluation of the processed tissue sections was determined by using a Nikon Eclipse 800 microscope.

Figure 4:
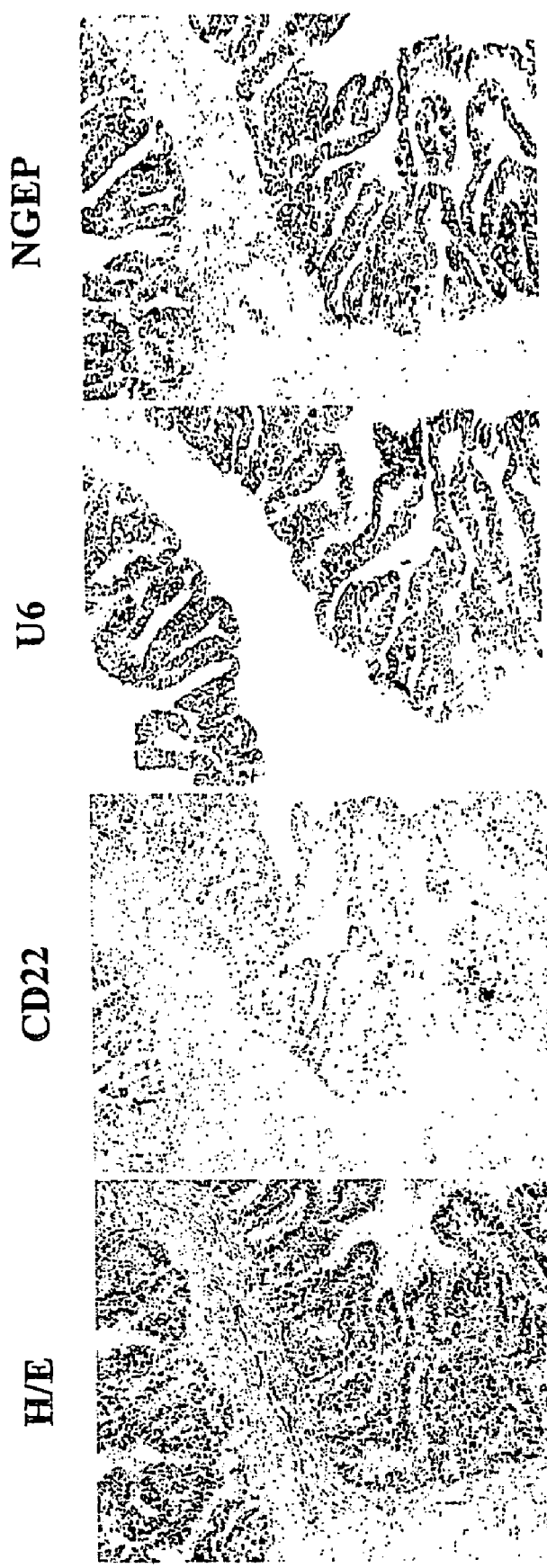
FIG. 4 is a set of digital images of in situ localization of NGEP mRNA in prostate tissue. The image labeled "H/E" is a digital image of a benign prostate section stained with H/E to show the morphology. The epithelial cells are stained blue while the connective tissue is pink. In the digital image labeled CD22, B lymphocyte specific gene CD22 used as a probe for negative control for in situ hybridization. Note the absence of signal in the epithelial cells. In the digital image labeled "U6," a small nuclear RNA was used as a probe for positive control of ill situ hybridization. The epithelial cells show a strong signal. In the digital image labeled "NGEP" a NGEP sequence was used as probe for localizing the region of its expression in the prostate tissue section. NGEP also shows strong signal in the epithelial cells.

As shown in FIG. 4, NGEP mRNA is highly expressed in prostatic epithelial cells of normal prostate and of prostate cancer specimens. There is no signal with a probe that does not contain the NGEP insert, indicating the specificity of the hybridization reaction. Also there was no detectable signal in cells in the stromal compartment of the tissue, indicating that NGEP is specifically expressed in the epithelial cells of the prostate. The signal intensity is comparable with the signal intensity of the positive control U6 probe. CD22, which is specifically expressed in B lymphocyte, was used as a negative control in the analysis.

Example 5

In vitro Transcription and Translation of the NGEP cDNA

The NGEP cDNA has a predicted open reading frame of 179 amino acids with a calculated molecular weight of 19.6 kDa. To determine the actual size of the protein encoded by the NGEP cDNA isolated, in vitro transcription and translation was performed using rabbit reticulocyte lysate system.

The complete NGEP transcript (SEQ ID NO:2), shown in FIG. 6, was cloned into pBluescript II SK (+) (Stratagene) and sequenced. The PCR product was directionally cloned into the pBluescript II SK (+) vector utilizing restriction sites in the primers. This was examined in an in vitro transcription coupled translation system using T7 RNA polymerase and rabbit reticulocyte lysate (TNT, Promega, Madison, Wis.). $^{35}$S-Met (ICN, Costa Mesa, Calif.) was incorporated in the reaction for visualization of translated products. The reaction was analyzed under reducing condition on a polyacrylamide gel (16.5% Tris/Tricine, Bio-Rad) together with a pre-stained marker (Life Technologies, Gaithersburg, Md.). The gel was dried and subjected to flurorography.

SDS-PAGE analysis and fluorography of the translated product showed (FIG. 5A) that the NGEP cDNA encodes a protein product of about 20 kDa in size (lane 2) and the size of the protein products from the in vitro transcription and translation experiment agree with the predicted open reading frames of the cDNAs.

To determine the size of the protein encoded by NGEP in cells and its subcellular localization in cells, LnCAP cells were transfected with a eukaryotic expression plasmid pcDNA3.1-Myc-His expressing NGEP with a Myc epitope tag at the carboxy terminus. LnCaP cells were maintained in RPMI medium 1640 (Quality Biologicals, Gaithersburg, Md.) at 37° C. with 5% CO2. The medium is supplemented with 10% fetal bovine serum (Quality Biologicals), 2 mM L-glutamine, 1 mM sodium pyruvate, and penicillin/streptomycin.

An eukaryotic expression plasmid pcDNA3.1-Myc-His expressing NGEP with a Myc epitope tag at the carboxy terminus was named pNGEP-Myc. pPATE-Myc was also used as a positive control for Myc epitope (Bera et al., ibid). The LnCAP cells were transiently transfected with these plasmids. After transfection, western blot analysis was done as described previously (Bera et al., ibid). Filters were probed with 200 ng/ml anti-Myc-tag monoclonal (9E10; Santa Cruz Biotech, Santa Cruz, Calif.).

Western blot analysis of cell extracts transfected with plasmid pcDNA3.1-Myc-His expressing NGEP using anti-myc antibody detects a band of 20 kDa (FIG. 5B, open arrow). In addition there is a high molecular weight band of about 24 kDa in size (FIG. 5B, closed arrow). Cell extracts transfected with pPATE-Myc-His (Bera et al., *Proc. Natl. Acad. Sci. USA* 99: 3058-3063, 2002) was used as positive control and the expected 16 kDa band is detected (lane pPATE-myc). No band was detected in untransfected cell extracts.

To determine the location of NGEP protein in the cell, immunocytochemistry was carried out in LnCAP cells transfected with plasmid pcDNA3.1-Myc-His expressing NGEP with a Myc epitope tag.

Co-transfection of pNGEP-Myc with pEGFP-C1 (Clontech) as a transfection marker was done in LnCAP cells. After 24 h incubation following transfection in a slide chamber, cells were fixed for 10 min in 4% formaldehyde, treated for 5 min with 0.2% triton X-100 in PBS for permeability, blocked for 30 min with 0.4% normal goat globulin and 0.1% saponin in PBS, then incubated at room temperature for 1 h with 5 µg/ml anti-Myc-tag monoclonal. Subsequently, the cells were incubated at room temperature for 1 h with TRITC-conjugated secondary antibodies (Jackson Laboratories, Bar Harbor, Me.) then mounted in anti-fade solution with DAPI (Vector Laboratories, Burlingame, Calif.). Labeled cells were analyzed by laser confocal microscopy.

It was first confirmed that neither transfection with pEGFP alone or immunostaining without anti-NGEP antibody showed positive signals of anti-Myc antibody, whereas green signals of GFP as a transfection marker were positive. As shown in FIG. 5C, immunostaining using anti-Myc antibody showed positive signals which are localized both in the cytoplasm and in the nucleus in LnCAP cells transfected with pNGEP-Myc (FIG. 5C). In about 5% of the transfected cells the red signals was found exclusively in the cytoplasm (FIG. 5D). The same results were obtained in PC3 and 293T cell lines. These data indicate that NGEP is localized in cytoplasm and nucleus and might be actively transported between nucleus and cytoplasm or enter the nucleus passively.

Thus, a new gene, NGEP, has been identified. NGEP is specifically expressed in prostate cancer and normal prostate cells. NGEP is localized at chromosome 2q37.3 on the human genome and has an open reading frame of 180 amino acids. The deduced amino acid sequence of NGEP has no sequence similarity with any known proteins in the database. RT-PCR analysis of NGEP expression in three established prostate cancer cell lines indicate that NGEP is expressed in androgen responsive LnCAP cells but not in either DU145 or PC3 cells which do not have androgen dependency. Genetically, loss of 2q has been reported in clinical samples of prostate cancer (for example see Cher et al., *Cancer Res.* 56: 3091-3102, 1996).

The NGEP cDNA has a predicted open reading frame of 179 amino acids with a calculated molecular weight of 19.6 kDa. Western blot analysis of NGEP transfected cells detect an expected 20 kDa protein product. In addition, an additional band of 26 kDa in size was detected in cell lysate transfected with NGEP (FIG. 4B, closed arrow). This 26 kDa product could be a phosphorylated form of NGEP. In fact, there are several predicted protein kinase phosphorylation sites in the NGEP sequence. The ExPAsy program predicts one cAMP-dependent protein kinase site at position 78-81 (KRGS); one protein kinase C phosphorylation site at position 138 (TxR); and three possible Casein kinase II phosphorylation sites at positions 72 (SppE), 138 (TwrE) and 142 (TflD). Because of its distribution in both cytoplasm and in the nucleus, NGEP could be a kinase itself.

Expression of NGEP is restricted to prostate cancer and normal prostate with no detectable expression in any normal essential tissues we have tested In situ hybridization experiments using a prostate cancer progression array showed that NGEP is expressed in more than 50% of the cancer specimens tested. Thus, NGEP can be used to detect prostate cancer, or as a target for immunotherapy.

Example 6

Radioimmunoassay to Detect NGEP

The following example sets forth an exemplary protocol for a radioimmunoassay to detect the presence NGEP in a sample.

Radiolabeling of NGEP

Two and a half micrograms of chemically synthesized or *E. coli* expressed NGEP are labeled with $^{125}I$ using the chloramine T method (Hunter and Greenwood, Nature 194:495, 1962). The labeled protein is then purified using a PD-10 column (Amersham Pharmacia Biotech).

Anti-NGEP Antibody

Anti-NGEP antibodies are prepared by using proteinA purified antisera from rabbits immunized with a *Pseudomonas* exotoxin (PE)-NGEP fusion protein using standard techniques (Bruggeman et al., BioTechniques 10:202, 1992).

Standard Curve

A standard curve is established by mixing a fixed amount of labeled NGEP (~0.2 ng at about 170 μCi/μg) with different concentrations of unlabeled NGEP (0.1 ng-50 ng) in 250 μl buffer (PBS with 0.25% bovine serum albumin) containing 1 μg of anti-NGEP antibody. The samples are incubated at room temperature for 4 hours. ProteinA sepharose beads are added and incubated for another hour. Finally the beads are collected by centrifugation and washed with buffer 3 times. The remaining bead pellet is measured for radioactivity in a gamma counter.

Sample Measurement

To measure the amount of NGEP in a tissue extract or a protein extract from a cell culture the same procedure is used, but with the sample substituted for the known amounts of the protein used in the standard curve description.

Example 7

Production of an Immune Response Against NGEP in a Primate

The prostate gland of the rhesus monkey is structurally and functionally similar to the human prostate (Wakui et al., *J. Anat.* 181:121, 1992; U.S. Pat. No. 6,165,460). Thus, juvenile male rhesus monkeys (Macaca mulatta), ages 1 to 2 years, are assigned to (e.g., three vaccination groups of four animals each, a low dose, a high dose and a control group). One animal from each group is surgically prostatectomized to parallel two situations with regard to potential therapy in humans: (a) prostate intact, with primary and/or metastatic disease; or (b) patients prostatectomized with prostate cancer metastatic deposits. Animals are immunized 3 times over a two month period with a recombinant virus (e.g. a pox virus, see U.S. Pat. No. 6,165,460). For example, a dose of either $1 \times 10^7$ or $1 \times 10^8$ PFU of a recombinant pox virus encoding NGEP is administered to 4 animals by skin scarification. A control vector (e.g. V-Wyeth, $1 \times 10^8$ PFU) is administered to a control group of animals.

Physical examinations are performed on ketamine (Ketamine® HCl, 10 mg/kg I.M.) sedated animals. Rectal temperatures and weights are recorded for each monkey on a weekly basis. The vaccination site is observed and erythema and swelling of the vaccination site are measured by caliper. Each animal is examined for regional lymphadenopathy, hepatomegaly, and splenomegaly. Any other gross abnormalities were also recorded.

Blood is obtained by venipuncture from the femoral vein of ketamine sedated animals before and after each immunization. A complete blood count, differential, hepatic and renal chemistry evaluation is performed on each monkey. Results are compared to normal primate values. Circulating levels of NGEP before and after immunization are analyzed (e.g by immunoassay or Northern blot).

Prior to each immunization and 2 weeks following each immunization, anti-NGEP antibody is quantified by ELISA. Microtiter plates are coated with purified NGEP (e.g. 100 ng/well,), ovalbumin (100 ng/well, Sigma), or $1 \times 10^7$ PFU/well UV-inactivated V-Wyeth in phosphate buffered saline (PBS). The plates are blocked (e.g. using 2% BSA in PBS), dried, and stored at −20° C. until used. The plates are incubated with serum (e.g diluted 1:5), as well as a monoclonal antibody for NGEP as a standard control, for 24 hours at 4° C. Plates are washed several times (e.g. with PBS containing 1%

BSA), and incubated with a commercially labeled antibody that specifically binds the anti-NGEP monoclonal antibody. An appropriate reagent system is used to visualize antibody binding. For example the antibody is labeled with horseradish peroxidase (HRP), and detected by HRP substrate system (Kirkegaard & Perry Laboratories, Gaithersburg, Md.) according to the manufacture's instructions. The absorbance of each well is read at 405 nm using a Bio-Tek EL310 microplate ELISA reader (Winooski, Vt.).

Sera from each monkey is analyzed by ELISA for immunoreactivity to NGEP. Sera obtained from monkeys prior to vaccination are also analyzed, and are negative for reactivity to NGEP. NGEP specific T-cell responses in monkeys immunized with NGEP containing vector or control vector are also analyzed using a lymphoproliferative assays using peripheral blood mononuclear cells.

Example 8

Kit for the Detection of Metastatic Prostate Cancer

Prostate cancer is known to metastasize to other areas of the body, such as bone. Antibodies to an NGEP polypeptide can be used to detect prostate cancer cells at locations other than the prostate.

In order to determine if a metastatic tumor originates in the prostate, the expression of NGEP is assessed. Specifically, a kit is utilized that provides an immunoassay that can be used to confirm that the cancer cells are of prostate origin.

A biological sample of the metastasis is obtained. In one example, the sample is a bone marrow sample. Non-specific immunoreactive sites on biological sample are blocked with a commercially available blocking agent, such as 10% bovine serum albumin in phosphate buffered saline (PBS), for thirty minutes at room temperature. The sample is then contacted with a mouse monoclonal antibody that specifically binds NGEP for an incubation period sufficient to allow formation of an immune complex (e.g. ten minutes to three hours at room temperature in a solution of 1%BSA). The presence of the immune complex (bound antibody) is detected by incubating the sample with a commercially available labeled secondary antibody that specifically binds the NGEP antibody. For example, a fluorescent labeled (e.g. fluorescein isothiocyanate, FITC) goat anti-mouse antibody is diluted 1:100 in PBS/1%BSA and incubated with the sample for an amount of time sufficient to form an immune complex (e.g. ten minutes to about two hours at room temperature). The samples are then processed to determine binding of the second antibody (e.g. detection of fluorescence). A positive signal indicates that the metastasis is of prostate origin.

Example 9

Activation of T Cells Using NGEP

Methods for evaluating immunogenicity of peptides are known. Immunogenicity be evaluated by, for example, evaluation of primary T cell cultures from normal individuals (see, e.g., Wentworth et al., *Mol. Immunol.* 32:603, 1995; Celis, et al., *Proc. Natl. Acad. Sci. USA* 91:2105, 1994; Tsai et al., *J. Immunol.* 158:1796 (1997); Kawashima et al., *Human Immunol.* 59:1 (1998)); by immunization of HLA transgenic mice (see, e.g., Wentworth et al., *J. Immunol.* 26:97, 1996; Wentworth et al., *Int. Immunol.* 8:651, 1996; Alexander, et al., *Immunol.* 159:4753, 1997), and by demonstration of recall T cell responses from patients who have been effectively vaccinated or who have a tumor; (see, e.g., Rehermann et al., *J. Exp. Med.* 181:1047, 1995; Doolan et al., *Immunity* 7:97, 1997; Bertoni et al., *J. Clin. Invest.* 100:503 (1997); Threlkeld, S. C. et al., J. Immunol. 159:1648 1997; Diepolder et al., *J. Virol.* 71:6011 1997).

In choosing CTL-inducing peptides of interest, peptides with higher binding affinity for class I HLA molecules can be utilized. Peptide binding is assessed by testing the ability of a candidate peptide to bind to a purified HLA molecule in vitro.

Based on the polypeptide sequence of NGEP, amino acid sequences bearing motifs for any particular HLA molecule can be identified. Peptides including these motifs can be prepared by any of the typical methods (e.g., recombinantly, chemically, etc.). Because NGEP is a self protein, the amino acid sequences bearing HLA binding motifs are those that encode subdominant or cryptic epitopes. Those epitopes are identified by a lower comparative binding affinity for the HLA molecule with respect to other epitopes in the molecule or compared with other molecules that bind to the HLA molecule.

Polypeptides that include an amino acid sequence from NGEP that, in turn, include an HLA binding motif also are useful for eliciting an immune response. This is because, in part, such proteins will be processed by the cell into a peptide that can bind to the HLA molecule and that have an NGEP epitope.

A complex of an HLA molecule and a peptidic antigen acts as the ligand recognized by HLA-restricted T cells (Buus et al., *Cell* 47:1071, 1986; Babbitt et al., *Nature* 317:359, 1985; Townsend and Bodmer, *Annu. Rev. Immunol.* 7:601, 1989; Germain, *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified (see, e.g., Southwood et al., *J. Immunol.* 160:3363, 1998; Rammensee et al., *Immunogenetics* 41:178, 1995; Rammensee et al., *J. Curr. Opin. Immunol.* 10:478, 1998; Engelhard, Curr. Opin. Immunol. 6:13 (1994); Sette and Grey, *Curr. Opin. Immunol.* 4:79, 1992).

Furthermore, x-ray crystallographic analysis of HLA-peptide complexes has revealed pockets within the peptide binding cleft of HLA molecules which accommodate, in an allele-specific mode, residues borne by peptide ligands; these residues in turn determine the HLA binding capacity of the peptides in which they are present (e.g., Madden, *Annu. Rev. Immunol.* 13:587, 1995; Smith, et al., *Immunity* 4:203, 1996; Fremont et al., *Immunity* 8:305, 1998; Stern et al., *Structure* 2:245, 1994; Jones, *Curr. Opin. Immunol.* 9:75, 1997; Brown, et al., *Nature* 364:33, 1993).

Accordingly, the definition of class I and class II allele-specific HLA binding motifs, or class I or class II supermotifs allows identification of regions within NGEP that have the potential of binding particular HLA molecules.

One method of identifying genes encoding antigenic determinants is as follows: Tumor infiltrating lymphocytes (TILs) from a subject with prostate cancer are grown and tested for the ability to recognize the autologous cancer in vitro. These TILs are administered to the subject to identify the ones that result in tumor regression. The TILs are used to screen expression libraries for genes that express epitopes recognized by the TILs. Subjects then are immunized with these genes. Alternatively, lymphocytes are sensitized in vitro against antigens encoded by these genes. Then the sensitized lymphocytes are adoptively transferred into subjects and tested for their ability to cause tumor regression. Rosenberg, et al., *Immunol. Today* 1997 18:175 (1997).

To ensure that NGEP elicits a CTL response to NGEP in vivo (or, in the case of class II epitopes, elicits helper T cells that cross-react with the wild type peptides), the NGEP can be used to immunize T cells in vitro from individuals of the appropriate HLA allele. Thereafter, the immunized cells' capacity to induce lysis of NGEP-sensitized target cells is evaluated.

More generally, NGEP peptides can be synthesized and tested for their ability to bind to HLA proteins and to activate HTL or CTL responses, or both.

Conventional assays utilized to detect T cell responses include proliferation assays, lymphokine secretion assays, direct cytotoxicity assays, and limiting dilution assays. For example, antigen-presenting cells that have been incubated with a peptide can be assayed for the ability to induce CTL responses in responder cell populations.

PBMCs can be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived.

A method which allows direct quantification of antigen-specific T cells is staining with Fluorescein-labeled HLA tetrameric complexes (Altman et al., *Proc. Natl. Acad. Sci. USA* 90:10330, 1993); Altman et al., Science 274:94,1996). Alternatively, staining for intracellular lymphokines, interferon-$\gamma$ release assays or ELISPOT assays, can be used to evaluate T-cell responses.

CTL activation may be assessed using such techniques known to those in the art such as T cell proliferation and secretion of lymphokines, e.g. IL-2 (see, e.g. Alexander et al., Immunity 1:751-761 (1994)).

In one specific, non-limiting example, transgenic mice that express a chimeric human class 1 major histocompatibility (MHC) class 1 molecule composed of the $\alpha$1 and $\alpha$2 domains of HLA-A2.1 and the $\alpha$3, transmembrane and cytoplamic domains of H2-kb HLA transgenic mice (see, e.g., Wentworth, P. A. et al., J. Immunol. 26:97, (1996); Wentworth, P. A. et al., Int. Immunol. 8:651 (1996); Alexander, J. et al., J. Immunol. 159:4753 (1997)) are immunized with plasmid DNA encoding NGEP. Specifically, each mouse is injected intramuscularly with 100 µg of plasmid five times every three weeks. After the final immunization CD8+ cells are partially purified using antibody-coated magnetic beads and re-stimulated with syngeneic spleenocytes for one week in T-stim media. Specifically cells from the immunized transgenic mice are co-cultured either with stimulating spleenocytes (e.g., $3.5 \times 10^6$ spleenocytes) pusled with various concentrations (100, 0.1 or 0.0001 µM) NGEP peptide or in the presence of free peptide (1 µM) in a 24 well plate containing 2 ml of a 1:1 mixture of RPMI1640 mdeia and Eagle-Hanks amino acid medium supplemented with L-glutamine, sodium pyruvate, non-essential amino acids, antibiotics (penicillin, streptomycin, $5 \times 10^{-5}$ M 2-mercaptoetanol, 10% fetal calf serum, and 10% T-stim (Collaborative Biomedical Products, Bedford, Mass.). On day seven, a cytoxoic T lymphocyte (CTL) assay is carried out using LnCAP cells expressing NGEP as target cells in the presence of peptides fragments of NGEP. For example, LnCAP target cells ($1 \times 10^6$) are labeled with 300 µCi of $Na_2^{51}CrO_4$ in 200-250 µl for 2 hours at 37° C. For test samples, targets are pulsed with peptide during labeling. Cells are then washed and added to wells along with the appropriate number of effector cells in 96-well round bottom plates. After four hours, supernatents are harvested and counted in an ISOMEDIC gamma counter (ICN). The mean of triplicate samples and percent of $^{51}Cr$ release is calculated (see Alexander-Miller et al, *Proc. Natl. Acad. Sci. USA* 93: 4102). The results demonstrate that NGEP peptides can be used to induce cytotoxic activity against LnCAP cells.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

We claim:

1. An isolated polypeptide comprising an amino acid sequence set forth as
SEQ ID NO:1.

2. A method for detecting prostate cancer in a subject, comprising
contacting a sample obtained from the subject with the antibody that specifically binds the polypeptide of claim 1 for a sufficient amount of time to form an immune complex;
detecting the presence the immune complex, wherein the presence of an immune complex demonstrates the presence of prostate cancer in the subject.

3. The method of claim 2, wherein the sample is a biopsy, blood, serum, or urine sample.

4. The method of claim 2, wherein the sample is a biopsy sample of non-prostate origin.

5. The method of claim 2, wherein the antibody is labeled.

6. A method for detecting a prostate cancer in a subject, comprising
contacting the sample with a labeled antibody that specifically binds the polypeptide of claim 1 for a sufficient amount of time to form an immune complex; and
detecting the presence of the immune complex thereby detecting the presence of the prostate cancer.

7. A pharmaceutical composition comprising a therapeutically effective amount of the polypeptide of claim 1 in a pharmaceutically acceptable carrier.

8. A polypeptide consisting of
the amino acid sequence set forth as SEQ ID NO:1.

9. A method for detecting a prostate cancer or a prostate cell in a subject, comprising
contacting the sample with an antibody that specifically binds the polypeptide of claim 8 for a sufficient amount of time to form an immune complex; and
detecting the presence of the immune complex, thereby detecting the prostate cell or the prostate cancer in the subject.

* * * * *